United States Patent [19]

Moore

[11] 4,427,366

[45] Jan. 24, 1984

[54] SCENTED CANDLE

[76] Inventor: Kenneth L. Moore, 2135 Oak Creek, San Antonio, Tex. 78232

[21] Appl. No.: 350,162

[22] Filed: Feb. 19, 1982

[51] Int. Cl.³ .............................................. F23D 13/16
[52] U.S. Cl. .................................... 431/291; 422/126
[58] Field of Search .................. 431/288, 289, 291; 422/126, 305

[56] References Cited

U.S. PATENT DOCUMENTS 3,385,649  5/1968  Hicks ..................................... 431/291
3,958,917  5/1976  Naz ....................................... 431/289

FOREIGN PATENT DOCUMENTS 45792  11/1966  German Democratic Rep. .... 431/288

Primary Examiner—Carroll B. Dority, Jr.
Attorney, Agent, or Firm—Cox & Smith Incorporated

[57] ABSTRACT

A scented candle comprising, in combination, a candle holder having vertically extending side walls of the type adapted to receive and encircle a candle, a wick cone centrally disposed within the candle holder, wherein the wick cone comprises a generally conically shaped candle having an integrally formed base adapted to centrally and firmly position the wick cone within the candle holder, and a plurality of odorizing chips formed of a mixture of candle wax and at least one scent producing material, the odorizing chips being disposed within the candle holder around the wick cone for controlled release of the scent producing material in response to the heat of the flame of the wick cone when the wick cone is lighted.

3 Claims, 4 Drawing Figures

SCENTED CANDLE

BACKGROUND AND SUMMARY OF THE INVENTION

The present invention relates to candles, and more particularly, to scented candles.

Prior to the present invention, scented candles have been produced by adding various scent producing materials to candle wax in the formation of the candle body. Although candles formed of such an admixture of candle wax and scent producing material have been effective for producing a fragrance, the fragrance of a particular candle cannot be altered to suit the individual taste of a consumer without replacing the candle. Indeed, the ability to change fragrances of a scented candle at will would be a decidedly superior advantage over prior art candles, and would enjoy the economical and desirable effect of prolonging the useful life of a particular candlestick.

Those advantages have been recognized in the art, for example as disclosed in U.S. Pat. No. 3,958,917 to Naz. U.S. Pat. No. 3,958,917 to Naz, however, attempted to solve the problem by placing a donut-shaped odorizer element about the lighted end of a candle.

The present invention offers a more desirable and economic solution. The present invention comprises, in combination, a candle holder having vertically extending side walls of the type adapted to receive and encircle a candle, a wick cone centrally disposed within the candle holder wherein the wick cone comprises a generally conically shaped vertically extending first candle body member having a candle wick extending substantially along the longitudinal axis thereof and having a base member formed integrally therewith. The base member is adapted to centrally and firmly position the wick cone within the bottom of the candle holder. A plurality of sculptured odorizing chips formed of a mixture of candle wax or paraffin material and at least one scent producing material are disposed within the candle holder around the wick cone. When the wick cone is lighted, the odorizing chips are heated and the aroma of the scent producing material is released. In the event a candle user wishes to change the fragrance, the user need only replace the odorizing chips in the candle holder.

Additionally, in the past, candle users have been stymied in their quest for individualized candle fragrances. Users have been limited in their fragrance selection to the particular fragrances chosen by the candle manufacturers. The present invention allows users to mix odorizing chips containing a variety of scent producing materials, thus arriving at a unique and individually pleasing aroma.

Also, scent producing compounds add impurities to the candle wax and cause a softening of the candle body. The melting point of the candle is thereby reduced leading to a shorter candle life and messier burning. Additional care must be taken in packaging, transporting and handling such candles. Consequently, candle manufacturers have generally attempted to strike a balance between the quantity of scent producing material used in relation to candle wax used to arrive at a compromise. Unfortunately, that compromise results in a softer candle which is, at best, inefficient at producing a fragrance.

The prior art attempted to solve the problem by forming an additional cavity in a candle body and inserting a columnar body impregnated with scent producing compounds in that cavity, for example as disclosed in U.S. Pat. No. 4,028,045 to Reiher. That, of course, leads to increased manufacturing costs.

The present invention obviates the problems of the past. The aforementioned wick cone may be formed from candle wax alone, thereby retaining the inherent hardness and melting point of candle wax. The odorizing chips may be formed with a high concentration of scent producing material, thus achieving a higher degree of fragrance in a particular burning time than was achievable using prior art techniques. The odorizing chips may be packaged, transported and sold in bags, and the softness of the chips themselves would have no effect. The chips are distributed about the wick cone in a candle holder, and thus their lower melting point would not shorten the life of the candle or render the candle messy to burn.

Accordingly, it is an object of the present invention to provide a new and useful scented candle.

It is another object of the present invention to provide a new and useful scented candle in which the scent producing material is added to the candle in the form of a plurality of odorizing chips.

Other objects, features, and advantages of the invention will become evident in light of the following detailed description, viewed in conjunction with the referenced drawings, of a preferred exemplary system according to the invention. The foregoing and following description of the invention is for exemplary purposes only. The true spirit and scope of the invention is set forth in the appended claims.

DESCRIPTION OF THE PREFERRED EMBODIMENT

Figure 1:
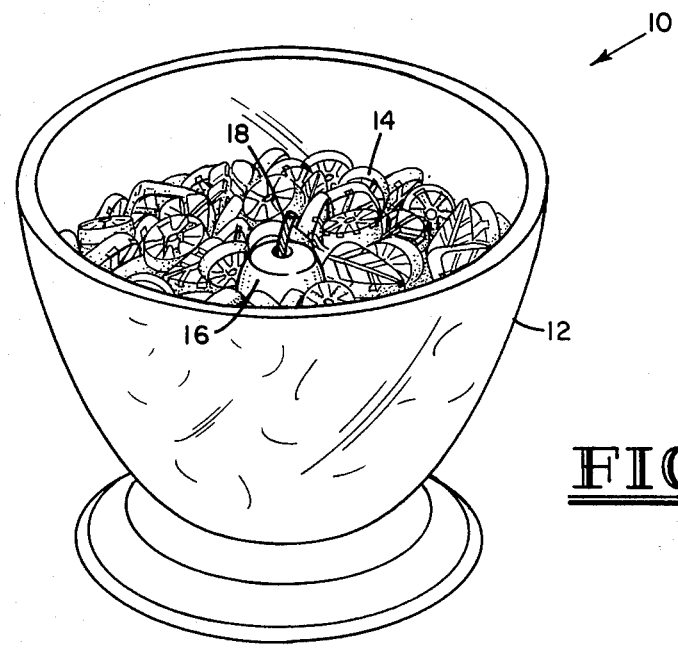
FIG. 1 is a perspective view of the scented candle of the present invention.

Referring to FIG. 1, an exemplary scented candle 10 includes a candle holder 12 having generally vertically extending side walls of the type adapted to receive and encircle a candle. Many such candle holders are available on the market and the shape of the candle holder per se forms no part of the invention. Candle holders 12 are typically formed of glass or a ceramic material.

In accordance with the invention, a wick cone 16 is centrally disposed within candle holder 12. As more clearly illustrated in FIG. 2, wick cone 16 has a generally conically shaped vertically extending first candle body member 19 and a base member 20. Wick cone 16 may be formed of standard commercial candle wax or parafin.

A candle wick 18 extends through and substantially along the longitudinal axis of wick cone 16.

The base 20 of wick cone 16 is chosen to approximate the internal diameter 21 of the base of candle holder 12. Thus the base 20 of wick cone 16 centrally and firmly positions wick cone 16 within candle holder 12.

Figure 3A:
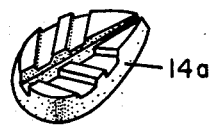
FIG. 3a is a perspective view of a sample odorizing chip used in the present invention.
Figure 3B:
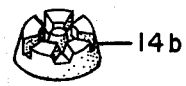
FIG. 3b is a perspective view of a sample odorizing chip used in the present invention.

Referring to FIGS. 3a and 3b, the odorizing chips 14 may be sculptured in the form of leafs 14a, flowers 14b or other desirable shapes. The odorizing chips are formed of a mixture of candle wax, parafin material or other heat responsive material and a scent producing material. Coloring agents which provide a different flame hue may also be used.

Figure 2:
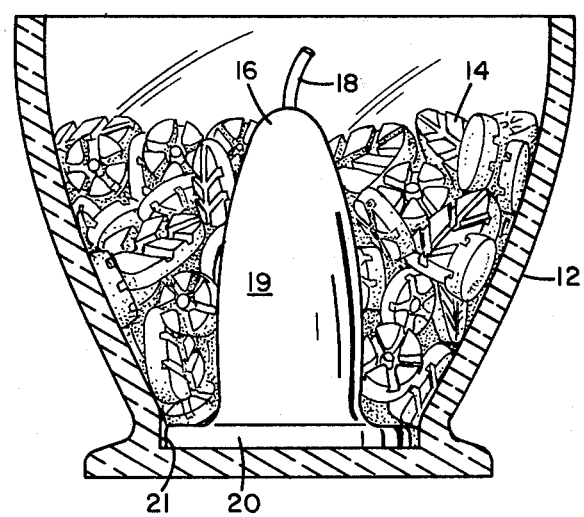
FIG. 2 is a cross-sectional view of the scented candle of the present invention.

Referring to FIG. 1 and FIG. 2, the scented candle, according to the present invention, operates as follows. The wick cone 16 is centrally disposed within candle holder 12 and a plurality of odorizing chips 14 placed in holder 12 around wick cone 16 and below the top thereof. When wick 18 is lighted, the odorizing chips 14 will be heated and the fragrance of the scent producing material released.

If the candle user wishes to change the fragrance, he or she need only replace odorizing chips 14 with chips bearing a new fragrance. Additionally, a candle user may combine a number of odorizing chips 14 having a variety of different fragrances, which fragrances will combine upon being heated to emit a unique, individualized scent.

Additionally, it can now be appreciated that because wick cone 16 is formed of candle wax without scent producing impurities added, wick cone 16 will burn at a much slower rate than scented candles in which the scent producing material is impregnated in the candle body. Moreover, as odorizing chips 14 melt, the resulting mass will be retained within holder 12, thus resulting in a messless candle.

It can, therefore, be seen that the present invention provides a new and useful scented candle which allows the candle fragrance to be changed at will and, indeed, a scented candle having a scent personally chosen and mixed by the candle user. Furthermore, it can be appreciated that the scented candle of the present invention provides all of the slow controlled burning advantages of non-scented candles, together with all of the additional advantages of scented candles. Moreover, it can be appreciated that the scented candle of the present invention provides for superior marketing ability in that candle merchants need not stock numerous shelves of limited selection scented candles, but can stock several varieties of odorizing chips and allow candle users to mix and match fragrances for their own choosing. Because the odorizing chips are preferably packaged, transported and sold in bags, the prior art problems of packaging, shipping and storing softened scented candles are eliminated.

Although the invention has been described in conjunction with the foregoing specific embodiment, many alternatives, variations and modifications will be apparent to those of ordinary skill in the art. Those alternatives, variations and modifications are intended to fall within the spirit and scope of the appended claims.

I claim:

1. A scented candle, in combination, comprising:
 a candle holder having vertically extending side walls of the type adapted to receive and encircle a candle and having a flat inner bottom;
 a wick cone centrally disposed within said candle holder, wherein said wick cone comprises a generally tapering vertically extending first candle body member formed of slow-burning candle wax and having a candle wick extending substantially along the longitudinal axis thereof and a flat base member formed integrally with said first candle body member and extending therefrom to substantially cover the flat inner bottom of said candle holder and adapted to allow users to centrally and firmly position said wick cone within said candle holder; and
 a plurality of molded oderizing chips of substantially uniform size formed of a faster-melting wax than said wick cone and at least one scent-producing material, said oderizing chips being disposed within said candle holder around said wick cone for controlled release of the scent-producing material in response to the heat of the flame of said wick cone when said wick cone is lighted.

2. A scented candle, in combination, as in claim 1 wherein said odorizing chips are saturated with at least one scent producing material.

3. A scented candle, in combination, as in claim 1 wherein said odorizing chips comprise a variety of chips having differing scent producing material.

* * * * *